(12) United States Patent
Kieser

(10) Patent No.: US 10,105,192 B2
(45) Date of Patent: *Oct. 23, 2018

(54) UNIQUE DEVICE IDENTIFICATION THROUGH HIGH DATA DENSITY STRUCTURAL ENCODING

(71) Applicant: SEMD HOLDINGS, LLC, San Antonio, TX (US)

(72) Inventor: Brian Kieser, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/848,484

(22) Filed: Dec. 20, 2017

(65) Prior Publication Data

US 2018/0132967 A1     May 17, 2018

Related U.S. Application Data

(63) Continuation of application No. 15/237,039, filed on Aug. 15, 2016, which is a continuation of application
(Continued)

(51) Int. Cl.
*G06K 7/00*      (2006.01)
*A61B 90/90*    (2016.01)
(Continued)

(52) U.S. Cl.
CPC ............ *A61B 90/90* (2016.02); *A61B 6/4494* (2013.01); *A61B 17/7004* (2013.01); *A61B 17/80* (2013.01); *A61B 17/866* (2013.01); *A61B 17/8625* (2013.01); *A61B 90/39* (2016.02); *A61B 90/96* (2016.02); *A61F 2/02* (2013.01); *A61F 2/442* (2013.01); *B33Y 80/00* (2014.12); *G06K 1/121* (2013.01); *G06K 7/10* (2013.01); *G06K 7/1099* (2013.01); *G06K 19/06* (2013.01); *H05K 999/99* (2013.01); *A61B 6/12* (2013.01); *A61B 8/0841* (2013.01); *A61B 2090/3966* (2016.02); *A61F 2250/0086* (2013.01); *A61F 2250/0089* (2013.01); *A61F 2250/0097* (2013.01); *A61F 2250/0098* (2013.01); *B29K 2995/0056* (2013.01); *B29L 2031/7532* (2013.01); *G06K 2019/06253* (2013.01); *G06K 2019/06271* (2013.01); *G06K 2215/0097* (2013.01)

(58) Field of Classification Search
CPC ........... G06K 7/00; G06K 19/00; G06F 17/00
USPC ................................ 235/453, 375, 487, 439
See application file for complete search history.

(56) References Cited

U.S. PATENT DOCUMENTS

2004/0024448 A1*  2/2004  Chang ..................... A61L 27/34
                                                              623/1.42
2010/0185285 A1*  7/2010  Perkins ................... A61F 2/442
                                                              623/17.11
(Continued)

*Primary Examiner* — Edwyn Labaze
(74) *Attorney, Agent, or Firm* — Buckingham, Doolittle & Burroughs, LLC

(57) ABSTRACT

An implant device identifiable after implantation comprises a main portion of the implant device and a coded portion of the implant device. The coded portion comprises a radiopaque element and indicia on the radiopaque element or indicia as a plurality of radiopaque elements disposed within the coded portion. The indicia are discernible by x-ray, fluoroscopy, computed tomography, electromagnetic radiation, ultrasound, or magnetic resonance imaging.

20 Claims, 10 Drawing Sheets

Related U.S. Application Data

No. 14/822,613, filed on Aug. 10, 2015, now Pat. No. 9,414,891, which is a continuation of application No. 14/302,171, filed on Jun. 11, 2014, now Pat. No. 9,101,321.

(60) Provisional application No. 61/938,475, filed on Feb. 11, 2014.

(51) Int. Cl.
| | |
|---|---|
| *A61B 6/00* | (2006.01) |
| *G06K 7/10* | (2006.01) |
| *G06K 1/12* | (2006.01) |
| *A61F 2/44* | (2006.01) |
| *A61F 2/02* | (2006.01) |
| *B33Y 80/00* | (2015.01) |
| *A61B 17/70* | (2006.01) |
| *A61B 17/80* | (2006.01) |
| *A61B 17/86* | (2006.01) |
| *A61B 90/96* | (2016.01) |
| *G06K 19/06* | (2006.01) |
| *B29L 31/00* | (2006.01) |
| *A61B 6/12* | (2006.01) |
| *A61B 8/08* | (2006.01) |
| *A61B 90/00* | (2016.01) |

(56) References Cited

U.S. PATENT DOCUMENTS

| | | | |
|---|---|---|---|
| 2012/0065503 A1* | 3/2012 | Rogers | A61L 31/18 600/431 |
| 2013/0053680 A1* | 2/2013 | Frey | A61B 6/12 600/411 |

* cited by examiner

UNIQUE DEVICE IDENTIFICATION THROUGH HIGH DATA DENSITY STRUCTURAL ENCODING

RELATED APPLICATION DATA

This application is a continuation of U.S. application Ser. No. 15/237,039 filed Aug. 15, 2016, which is a continuation of U.S. application Ser. No. 14/822,613, filed Aug. 10, 2015, which is a continuation of U.S. application Ser. No. 14/302,171, filed Jun. 11, 2014, which claims the priority benefit of U.S. Provisional Application Ser. No. 61/938,475, filed Feb. 11, 2014, which are hereby incorporated in their entirety herein by reference.

FIELD OF THE INVENTION

The present invention relates to identifiable implants, methods of identifying implants, and systems for identifying implant devices.

BACKGROUND OF THE INVENTION

Medical implant devices used in surgical procedures can be associated with particular information to guide medical professionals before and after the surgical procedure. Each implant device carries a wealth of information that is valuable to the patient, the implant manufacturer, medical researchers, healthcare professionals, and medical facilities. However, the information, which may include the implant manufacturer and manufacturer's lot number, the date and location of surgical implantation, the responsible surgeon, any medical notes, photographs, or diagrams relating to the implant, surgery, or condition, may not be adequate, properly recorded, or readily accessible for beneficial use by a healthcare professional, implant manufacturer, or medical researcher after implantation. Problems relating to poor implant records can lead to unnecessary delay or even medical error by healthcare professionals. Moreover, there are many different implant identification methods currently in place instead of a common system to allow manufacturers, distributors, and healthcare facilities and professionals to effectively track, identify, and manage implant devices and medical device recalls. The U.S. Food and Drug Administration recently announced a program focusing on requirements for unique device identifiers for every medical implant device to address the need for a more robust implant device identification system, the details of which are incorporated by reference herein: www.fda.goviudi.

SUMMARY OF THE INVENTION

In accordance with an aspect of the invention, an implant device identifiable after implantation is provided comprising a main portion of the implant device and a readable portion of the implant device. The readable portion may comprise a radiopaque element and indicia disposed on at least one surface thereof or disposed within the implant. The indicia may include a plurality of modifications to at least one surface of the radiopaque element or a plurality of radiopaque elements disposed within the readable portion such that the indicia are discernible by at least one of x-ray, fluoroscopy, computed tomography, electromagnetic radiation, ultrasound, and magnetic resonance imaging.

In accordance with further aspects of the invention, the readable portion may be integral with the main portion. The readable portion may also be disposed upon the main portion. The plurality of modifications may include an array of holes in the at least one surface of the radiopaque element. The plurality of modifications may include an array of notches or variations of density in the at least one surface of the radiopaque element. The array of notches in the at least one surface of the radiopaque element may form at least one bar code. The at least one bar code may comprise a Hamming code. The plurality of modifications may be less than or equal to two centimeters in length.

In accordance with further aspects of the invention, a system for identifying an implantable device is provided comprising an implantable device comprising a main portion and a readable portion. The readable portion may comprise a radiopaque element and indicia disposed on at least one surface thereof. The indicia may include a plurality of modifications to at least one surface of the radiopaque element or a plurality of radiopaque elements disposed within the readable portion. The indicia may further include a database containing a plurality of records associated with a plurality of implantable devices and a user interface comprising means for displaying information associated with the indicia based on the plurality of records. The indicia may be discernible by at least one of x-ray, fluoroscopy, ultra-sound computed tomography, electromagnetic radiation, ultrasound, and magnetic resonance imaging.

The plurality of modifications may include an array of holes in the at least one surface of the radiopaque element. The plurality of modifications may include an array of notches in the at least one surface of the radiopaque element. The array of notches in the at least one surface of the radiopaque element may form at least one bar code. The at least one bar code may comprise a Hamming code.

In accordance with further aspects of the invention, a method of identifying a micromanufactured implant device is provided comprising discerning indicia by at least one of x-ray, fluoroscopy, computed tomography, electromagnetic radiation, ultrasound, and magnetic resonance imaging. The indicia may include a plurality of modifications to at least one surface of a radiopaque element or a plurality of radiopaque elements disposed within a readable portion. The method of identifying a micromanufactured implant device may further comprise accessing a plurality of records associated with at least one of a plurality of implantable devices and providing information associated with the micromanufactured implant based on the indicia and the plurality of records. As used herein, the term "micromanufactured" encompasses all microfabrication techniques such as additive manufacturing and micromachining, and use of this term is not intended to limit the size or scale constraints or the type of the manufacturing process in any way. The term is used to elucidate the desire for the detectable portion of the implant device of the present invention to be either an incorporated portion of an implant or of a size capable of being implanted.

In accordance with further aspects of the invention, the method of identifying a micromanufactured implant device may further comprise displaying information associated with the micromanufactured implant based on the indicia and the plurality of records through a user interface. The user interface may be a reader capable of reading indicia and may include a display to display information relating to indicia. The readable portion may be disposed upon a main portion of the micromanufactured implant device. The plurality of modifications may include an array of holes in the at least one surface of the radiopaque element. The plurality of modifications may include an array of notches in the at least one surface of the radiopaque element. The array of notches in the at least one surface of the radiopaque element may form at least one bar code. The at least one bar code may comprise a Hamming code or other similar methods for error detection and correction that are known in the coding theory art. Additionally, data compression may be used in the coded indicia of the preferred embodiment.

In accordance with further aspects of the invention, an implant device identifiable after implantation is provided comprising a main portion of the implant device and a readable portion of the implant device. The readable portion may comprise a plurality of laminae or laminar planes (a finite planar volume). Each of the laminae, hereafter referred to as "laminar planes," may comprise separately readable indicia such that the indicia may be discernible in three dimensions by at least one of x-ray, fluoroscopy, computed tomography, electromagnetic radiation, ultrasound, and magnetic resonance imaging.

The readable portion may be integral with the main portion. Also, the readable portion may be disposed upon the main portion. Further, the indicia may include an array of voids on or in a corresponding laminar plane of the readable portion. The indicia may include an array of embedded markers on or in a corresponding laminar plane of the readable portion. The embedded markers may comprise a modulation of material compositions such that a first material composition of at least one first embedded marker is different than a second material composition of at least one second embedded marker. Further, the indicia may include a first array of embedded markers on or in a first laminar plane of the readable portion and a second array of embedded markers on or in a second laminar plane of the readable portion. The first array may comprise a first embedded marker having a first material composition different than a second material composition of a second embedded marker disposed in the second array. The indicia may comprise information in the form of a code. The code may comprise a Hamming code or other similar methods for error detection and correction that are known in the coding theory art. Additionally, data compression may be used in the coded indicia of the preferred embodiment.

In accordance with further aspects of the present invention, a method of manufacturing an identifiable implant device is provided comprising providing a main portion of the implant device, providing a readable portion of the identifiable implant device, printing a first material onto a first readable portion surface to create a first printed layer, and printing the first material onto the first printed layer to create a second printed layer. The printing of the first material onto the first readable portion surface or the printing of the first material onto the first printed layer may comprise printing encoded indicia. The encoded indicia may comprise voids in the first material or measurable variations in density. The method of manufacturing an identifiable implant device may further comprise printing a second material onto at least one of the first readable portion surface and the first printed layer, such that the encoded indicia comprises the second material.

In accordance with further aspects of the present invention, an implant device identifiable after implantation is provided comprising a main portion of the implant device and a readable portion of the implant device. The readable portion comprises an internal structure inside the readable portion. The internal structure comprises a plurality of linking structures. Each of the linking structures has a predetermined size or orientation. The linking structures are interconnected to substantially form the internal structure. The linking structures form predetermined indicia such that the indicia are discernible by x-ray, fluoroscopy, computed tomography, electromagnetic radiation, ultrasound, and/or magnetic resonance imaging. The readable portion may be integral with the main portion or disposed upon the main portion. The indicia in the readable portion of the implant device may comprise a Hamming code or other similar methods for error detection and correction that are known in the coding theory art. Additionally, data compression may be used in the coded indicia of the preferred embodiment.

BRIEF DESCRIPTION OF THE FIGURES

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
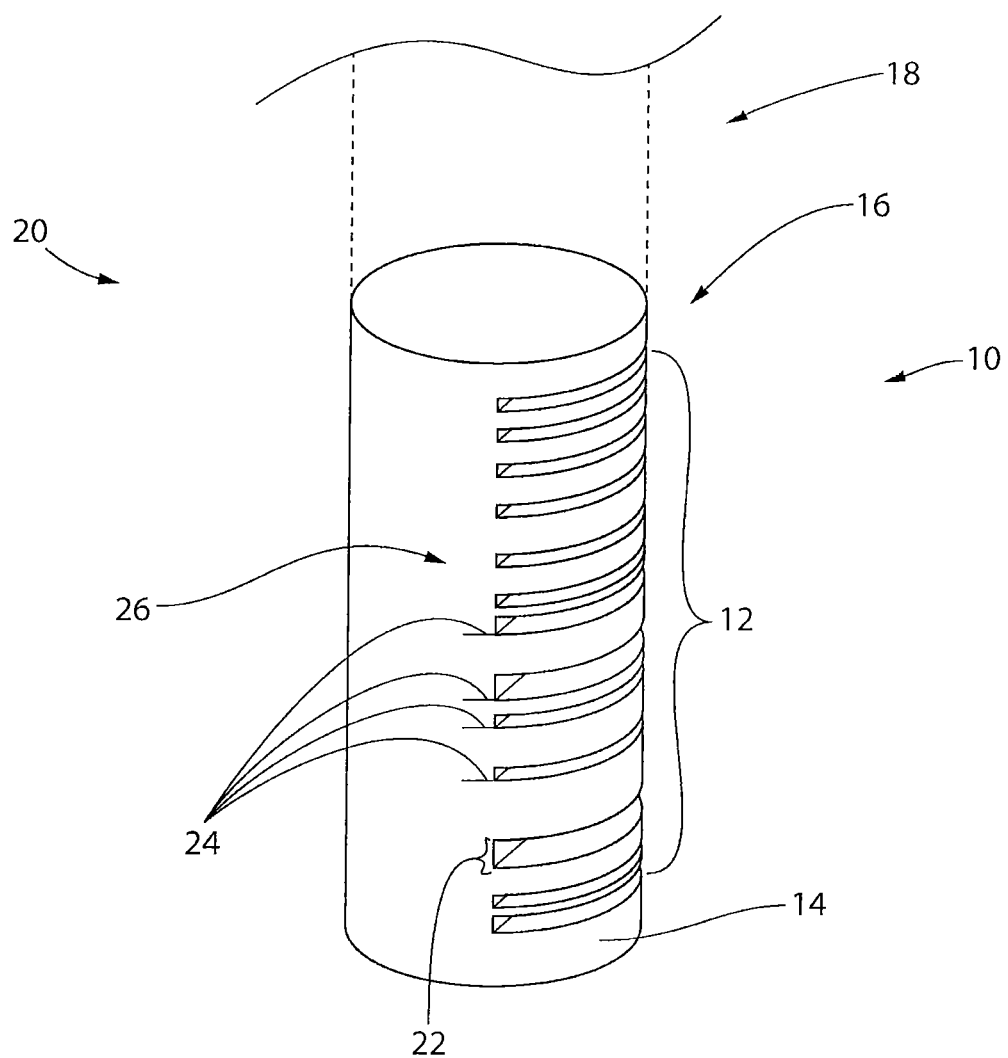
FIG. 1 is a side perspective view of a micromanufactured identifiable implant device in accordance with aspects of the present invention.

Reference is now made to FIG. 1, which shows an implantable rod structure 10 having a series of notches 12 in one longitudinal side 14 of the rod structure 10. The implantable rod structure 10 of the preferred embodiment of FIG. 1 features a readable portion 16 shown in FIG. 1 to be integral with a main portion 18 of an implant device 20. Alternatively, the readable portion 16 of the implant device 20 may be disposed upon the main portion 18 of the implant device 20. The readable portion 16 may be coupled to the main portion 18 by such means as fasteners or adhesives or through interference fit. Each of the notches 12 is a modification to the surface of the readable portion 16, has a predetermined width 22, and is located at a predetermined axial position 24 so as to create indicia 26 representing one-dimensional data. The rod structure 10 in the preferred embodiment is a radiopaque structure, such as a tantalum rod. As will be further described below, the rod structure 10 may have a variable density such that the rod structure contains indicia in the form of a variable density internal structure or a particular mesh structure created by additive manufacturing, thereby increasing the density of data coding. After implantation, the rod structure 10 and indicia 26 are detectable and readable via a variety of methods such as x-ray, fluoroscopy, computed tomography, electromagnetic radiation, ultrasound, and magnetic resonance imaging. The indicia 26 is detected and received by conventional medical imaging devices. Imaging software, preferably high resolution imaging software, then reads the data from the indicia 26 to decode and store and/or display the information from the implant device 20.

In a first embodiment of the present invention, the data represented by the indicia 26 on the surface of the rod structure 10 references unique information located in an external database. One example of such information includes data from the indicia 26 representing a unique numerical identifier corresponding to a wealth of manufacturer, patient, surgeon, or surgical procedure information located in an external healthcare facility database.

In further embodiments of the present information, the size of the indicia may be decreased, and the density of the data thereby increased, such that additional information beyond mere reference data may be recorded onto the surgical implant. Such embodiments are further discussed below.

In the preferred embodiment of the present invention, error correction is used to increase the resolution of the imaging technology, thereby allowing an increase in data density. Error correction is discussed in more detail below.

Figure 9:
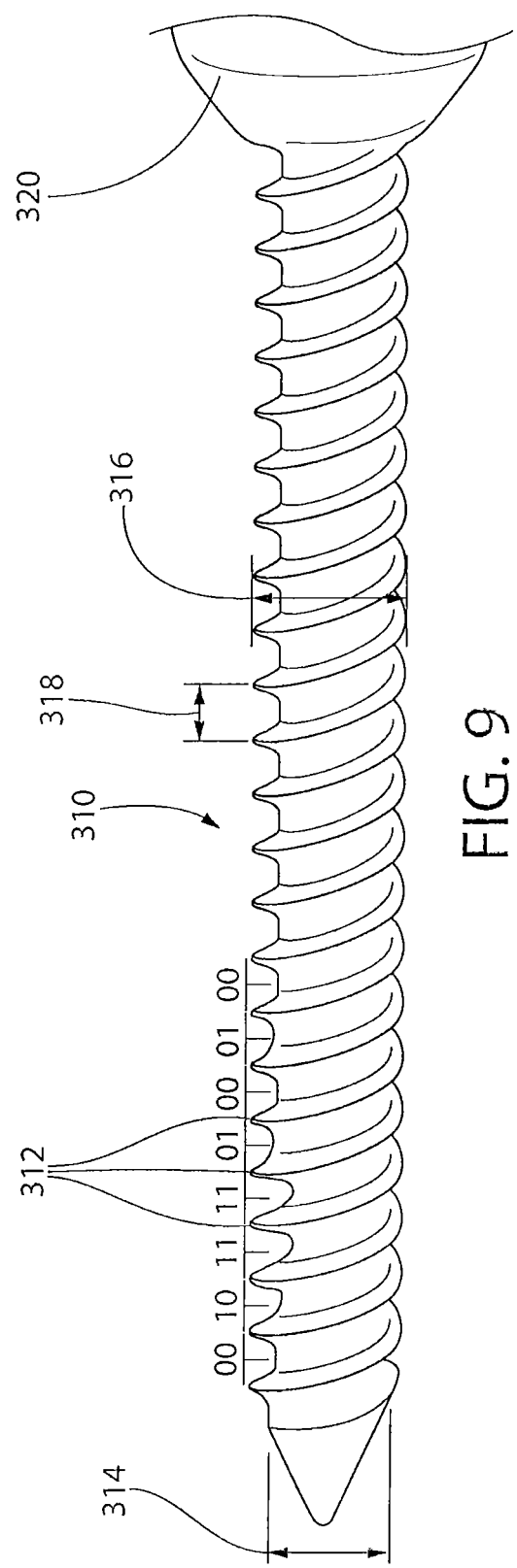
FIG. 9 is a side perspective view of a micromanufactured identifiable implant device in accordance with further aspects of the present invention.

Referring now to FIG. 9, rod structure 310 includes a plurality of threads 312 in a spiral or helical configuration around the circumference of the rod structure 310. Although the threads 312 shown in FIG. 9 are continuous to form a screw structure, such as a pedicle screw, the inner diameter 314 between adjacent threads 312 is varied to form indicia. As indicated in FIG. 9, the predetermined indicia allow coded data to appear within the functional structure of the rod structure 310 before and after implantation. Alternatively, the outer diameter 316 of threads 312 may be varied in addition to, or instead of, the variation of the inner diameter 314 to retain coded indicia on the rod structure 310. Further, the axial spacing 318 between adjacent threads 312 may be varied in order to store data. Even further, the particular shape of the spacing between adjacent threads 312, such as a square, triangular, or circular shape, may also allow data storage in the rod structure 310. A variation of this embodiment includes a micromanufactured implant device having indicia in or on the head 320 of the rod structure 310, such as coded indicia in the head of a surgical screw.

Any of the embodiments, including each particular structure, disclosed in the present application may include encoded implant devices having the forms of, or being incorporated into, screws, rods, or other medical devices such as shoulder implants, hip implants, knee implants, or cardiovascular devices, stents, etc. One such example of a structure and related method of the present invention may be one or more structurally encoded tantalum rod(s) in a PEEK interbody cage assembly.

Figure 2:
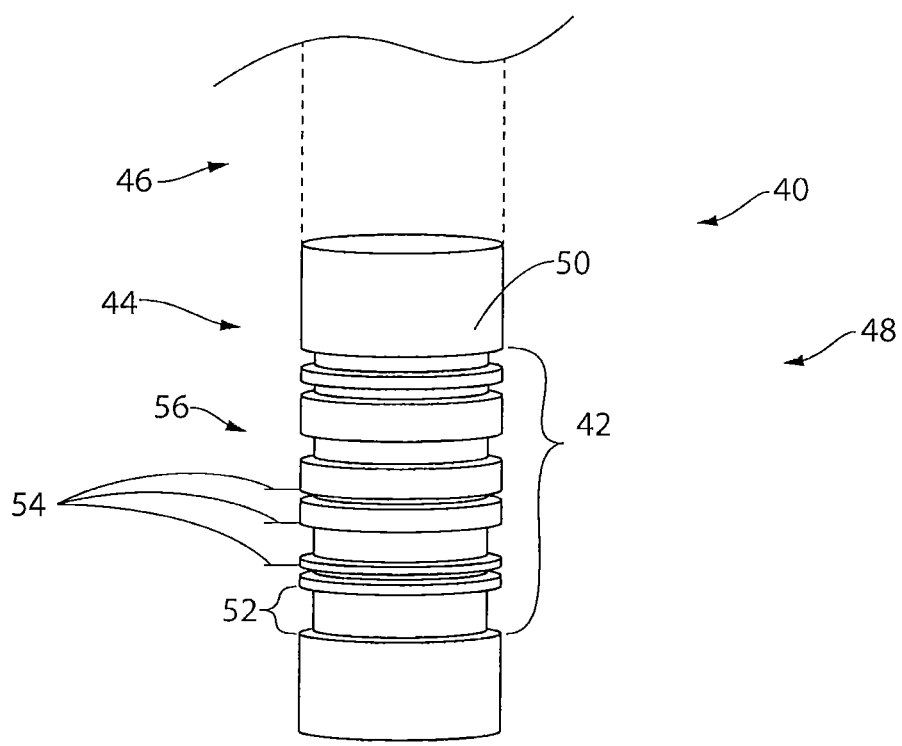
FIG. 2 is a side perspective view of a micromanufactured identifiable implant device in accordance with further aspects of the present invention.

Referring now to FIG. 2, an implantable rod structure 40 of a preferred embodiment of the present invention features a series of notches 42 around the circumference of the rod structure 40. The implantable rod structure 40 of the preferred embodiment of FIG. 2 features a readable portion 44 shown in FIG. 2 to be integral with a main portion 46 of an implant device 48. Alternatively, the readable portion 44 of the implant device 48 may be disposed upon the main portion 46 of the implant device 48. The readable portion 44 may be coupled to the main portion 46 by such means as fasteners or adhesives or through interference fit. Each of the notches 42 is a modification to an exterior surface 50 of the readable portion 44, has a predetermined width 52, and is located at a predetermined axial position 54 so as to create indicia 56 representing one-dimensional data. The rod structure 40 in the preferred embodiment is a radiopaque structure, such as a tantalum rod. After implantation, the rod structure 40 and indicia 56 are detectable and readable via a variety of imaging methods such as x-ray, fluoroscopy, computed tomography, electromagnetic radiation, ultrasound, and magnetic resonance imaging. The notches 42 of the preferred embodiment may be created using known lathe (machining) techniques or through additive manufacturing processes, as further discussed below. As opposed to indicia located only on a side of a rod structure as shown in FIG. 1, positioning of indicia 56 around the circumference of the rod structure 40, as shown in FIG. 2, increases visibility of the indicia 56 and readability of the data by imaging methods. The indicia 56 is detected and received by medical imaging devices, which transmits the data to imaging software with sufficient resolution for accurately resolving the indicia. The imaging software reads the indicia 56 to decode and store and/or display the information from the implant device 48.

Although the indicia 26 and 56 shown in FIGS. 1 and 2 is oriented in a direction perpendicular to the axis of the rod structures 10 and 40, the indicia of the rod structures 10 and 40 may be oriented in a skewed or slanted orientation such that the indicia is not perpendicular to the axis of the rod structures 10 and 40. As will be recognized by one having ordinary skill in the art, any embodiment of the exemplary rod structures shown in FIGS. 1-3 and 9 may include notches, threads, or similar surface modification. Furthermore, each notch, thread, or similar structure may vary in depth, cross-section, or geometric shape across the series or array for further data storage.

With regard to the rod structures 10 and 40, one exemplary use of the rod structures described in the present invention is in spine fusion. The rod structures may be utilized in spinal cages classified by the FDA as Cement Restrictors, Vertebral Body Replacement Devices (VBR), or Interbody Fusion Devices (IBFD). Another variation of the present invention is not limited to rod structures used in spinal cages and may include the use of rod structures in allograft bone and other implantable medical devices. This embodiment of the implant device of the present invention may include donor information such as tissue identification number, donor number, or sterility information. As will be fully understood by the present invention, such encoding can be accomplished quickly before implantation.

In a preferred embodiment of the present invention, the data represented by the indicia 56 on the surface of the rod structure references unique information located in an external database. One example of such information includes the data from the indicia 56 representing a unique implant number corresponding to a wealth of manufacturer, patient, surgeon, or surgical procedure information located in an external healthcare facility database.

Error correction is used in a preferred embodiment of the present invention to increase the resolution of the imaging technology, thereby allowing an increase in data density for a given measurement technology. By encoding, for example, a number into the implant through micro-machined holes and/or notches, sufficient permutations of the code can be recorded. In a preferred embodiment of an implantable device according to the present invention, a tantalum marker used in polymer spine implants contains, for one example, 400 micron discrete notches. The full code width and the bit count could, in this example, be dictated by machining precision and accuracy, number of variable machining widths (e.g., 100 microns, 200 microns, and 300 microns), total bar length, and image resolution. To ensure robustness in the encoding scheme, error correction in the form of a Hamming code is implemented in the preferred embodiment but any error correction method known in the coding theory art could be employed. In the preferred embodiment shown in FIGS. 1 and 2, four variable width notches every 250 microns allow eight bits of data to be encoded reliably every millimeter and read by a computed tomography scan with sufficient resolution to identify the notches. This is an example under the preferred embodiment having values that are "power of 2 friendly" in order to clarify one embodiment of the present invention. The specific values of any particular embodiment of the present invention depend upon the imaging and manufacturing resolution, which will improve over time, as one having ordinary skill in the art may recognize.

Figure 3:
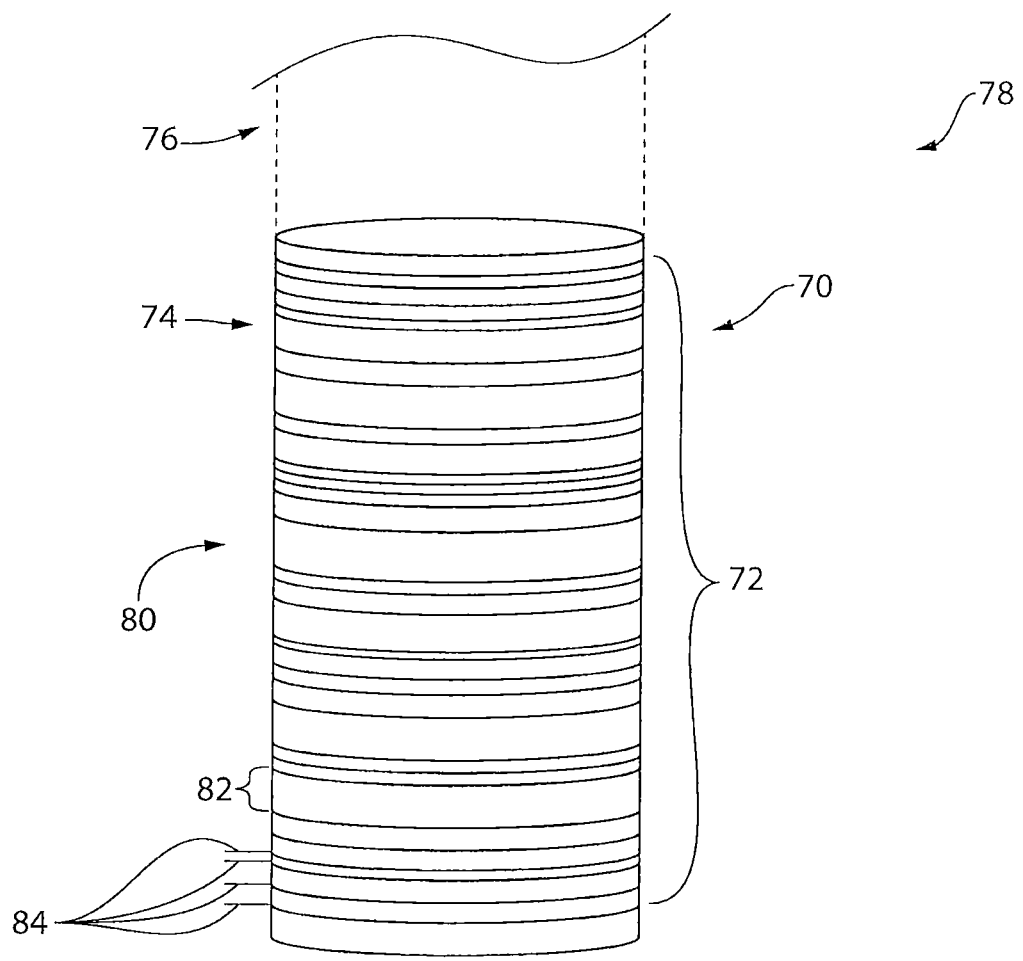
FIG. 3 is a side perspective view of a micromanufactured identifiable implant device in accordance with further aspects of the present invention.

Referring now to FIG. 3, an implantable rod structure 70 of a preferred embodiment of the present invention features multiple materials in discrete layers 72 to create one-dimensional data around the circumference of the rod structure 70. The implantable rod structure 70 of the preferred embodiment of FIG. 3 features a readable portion 74 shown in FIG. 3 to be integral with a main portion 76 of an implant device 78. Alternatively, the readable portion 74 of the implant device 78 may be disposed upon the main portion 76 of the implant device 78. The readable portion 74 may be coupled to the main portion 76 by such means as fasteners or adhesives or through interference fit. Similar to the notched indicia shown in FIGS. 1 and 2, the variance of material across the layers 72 in the embodiment shown in FIG. 3 creates indicia 80 representing data that is readable across the axial dimension of the rod structure 70. Alternative embodiments may feature multiple material layers readable across a different dimension or a structure having a different shape constructed using layers of multiple materials.

Referring again to the preferred embodiment of FIG. 3, each of the distinct material layers 72 has a predetermined width 82 and is located at a predetermined axial position 84 so as to create the indicia 80 representing one-dimensional data. At least one of the layers 72 in the rod structure 70 of FIG. 3 is a radiopaque structure. In the preferred embodiment each of the layers 72 is composed of a particular material having some degree of opacity. Like the rod structures of FIGS. 1 and 2, after implantation, the rod structure 70 and indicia 80 of the implant device 78 of FIG. 3 are detectable and readable via a variety of imaging methods such as x-ray, fluoroscopy, computed tomography, electromagnetic radiation, ultrasound, and magnetic resonance imaging. The indicia layers 72 of the preferred embodiment shown in FIG. 3 are structured so as to be visible from any side of the rod structure 70 to increase readability of the data by imaging methods. The indicia 80 are detected and received by medical imaging devices, which transmits the data to imaging software, preferably high resolution imaging software. The high resolution imaging software reads the indicia 80 to decode and store and/or display the information from the implant device 78.

The information or data encoded onto or into the implant devices of the embodiments disclosed in the present invention may be detected, decoded, read, transferred, stored, displayed, or processed according to such methods and devices disclosed in U.S. Pat. No. 8,233,967 or U.S. Patent Application Publication No. 2013/0053680, both of which are incorporated herein by reference.

The implantable device 78 of FIG. 3 is manufactured using additive manufacturing (AM) techniques. Due to their precision and programmability, AM processes may be used for any of the embodiments shown in FIGS. 1-3 to allow a reduction in the size of the indicia and, therefore, increased density of data included onto the surface of the implantable rod structure. In some cases, machining may be sufficient to provide the indicia necessary for the implantable rod structure. With increased data density, additional information beyond mere reference data may be recorded onto the surgical implant 78. The data recorded onto the implant device itself may include the manufacturer, patient, surgeon, or surgical procedure information that would otherwise need to be stored in and accessed through an external database. Additionally, AM allows complex, mass customized, internal structures otherwise unavailable with conventional manufacturing, including three-dimensional structures discussed in further detail below. Moreover, AM eliminates the need for tooling and can therefore allow fabrication of implants with unique identifiers within the structure with no additional masks, molds or user interaction.

ASTM International formed Committee F42 on Additive Manufacturing Technologies in 2009 with the mission of setting the standards for design, process, and materials with regards to AM. The committee defined a taxonomy of seven sub-technologies that together constitute the full suite of AM techniques. The seven sub-technologies are described in ASTM F2792-12a, the details of which are incorporated by reference herein.

Material extrusion is an additive manufacturing process where material is selectively dispensed through an extrusion nozzle. The most common implementation of this method involves the extrusion of thermoplastic material through a heated orifice. The materials available for the most common implementation tend to be functional plastics that are sufficiently robust to withstand harsh environments such as chemical, mechanical, or temperature exposure.

Vat photo polymerization features a vat of liquid photo curable polymer that is selectively cured with an energy source such as a laser beam or other optical energy. The part is typically attached to a platform that descends one cure depth after a layer is completed and the process is repeated. This class of additive manufacturing benefits from feature sizes dictated by either the laser beam width or optical resolution in the X and Y axis and minimum cure depth in Z.

Powder bed fusion processes include selectively melting or sintering a layer of powder using an energy source such as a laser or electron beam, lowering the layer by a fabrication layer thickness, and adding a new powder layer by delivery with a rake or roller and material storage mechanism. The process continues with the next layer. Unmelted powder in the bed acts inherently as support material for subsequently built layers.

Material jetting uses ink-jetting technology to selectively deposit the build material with a cure prior to the application of subsequent layers. An exemplary version of this technology may be ink jetting multiple photo-curable polymers and follow the inkjet head with a UV lamp for immediate and full volume curing. With multiple materials, fabricated items can be multi-colored or materials can be chosen with varying stiffness properties. Ink jetting is also naturally well suited for parallelism and thus can be easily scaled to larger and faster production.

Binder jetting includes selectively ink jetting a binder into a layer of powder feedstock. Additional powder material is then dispensed from a material storage location by a rake or roller mechanism to create the next layer. Some binder jetting technologies may require a post-anneal furnace cycle depending on the materials being used (e.g., metals, ceramics). One exemplary system may inkjet color (much like a commercial inkjet color printer) in addition to the binder into a powder, and may therefore provide structures with colors throughout the structure for conceptual models. Another binder jetting system may utilize a post anneal process to drive out the binder to produce metal or ceramic structures.

Sheet lamination is another additive manufacturing process in which individual sheets of material are bonded together to form three-dimensional objects. In one exemplary embodiment, sheets of metal are bonded together using ultrasonic energy. The process has been shown to produce metallurgical bonds for aluminum, copper, stainless steel, and titanium. A subsequent subtractive process between layers adds internal structures and other complex geometries impossible with conventional subtractive manufacturing processes that start from a billet of material.

Directed energy deposition is another additive manufacturing process that directs both the material deposition and the energy source (typically a laser or electron beam) at the surface being built. Directed energy deposition processes typically use powder or wire-fed metals and exemplary applications of the process may include repair of high value components used in aircraft engines.

The implant device of the present invention may be manufactured by conventional methods such as a machining operation using any milling, lathe, or drilling operation to include standard machining and fabrication methods known in the art of manufacturing medical implants.

The embodiments of FIGS. 1-3 show an implantable rod structure having a length of one centimeter. Exemplary embodiments of each implant device shown in FIGS. 1-3 include each notch or material variation having a thickness of 0.1-0.3 millimeters, which results in storage of about 30-40 bits of information on the implantable rod structure. After utilizing bits for Hamming code error correction, about 25-35 actual data bits create approximately 30 million to 30 billion indexing options into an external database or for limited information stored on the implant such as an implant expiration date and lot number.

Figure 4:
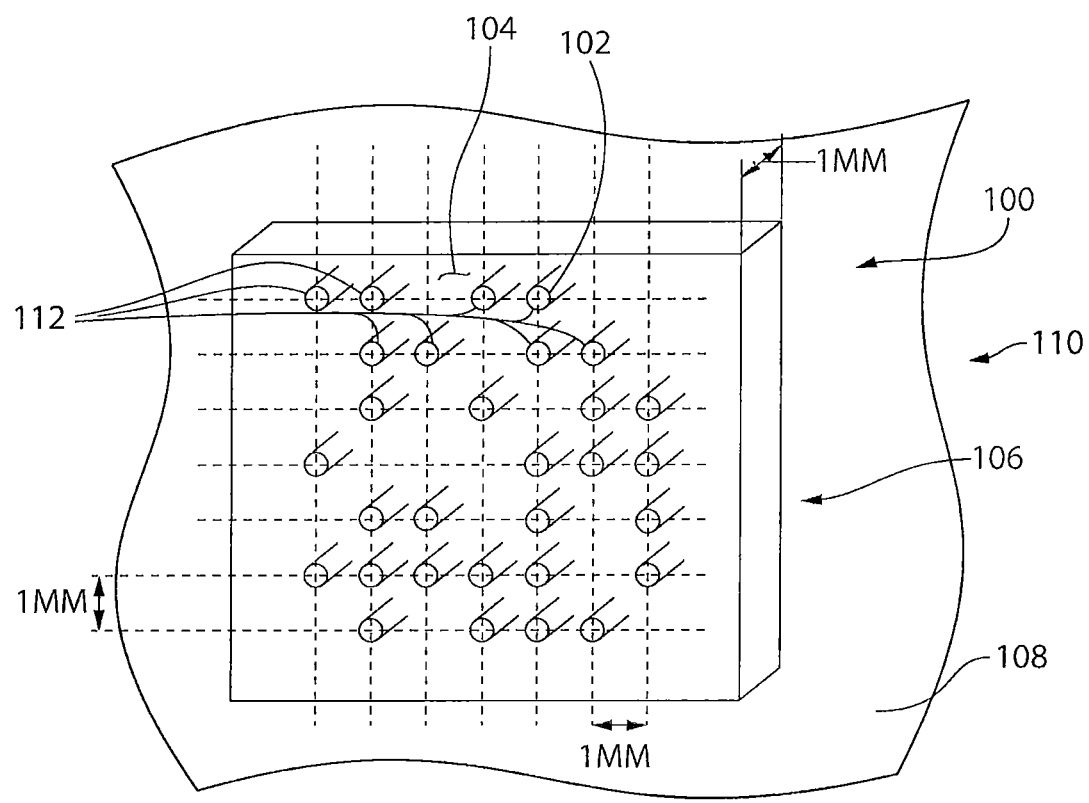
FIG. 4 is a front perspective view of a micromanufactured identifiable implant device in accordance with further aspects of the present invention.

Referring now to FIG. 4, an implantable plate structure 100 of a preferred embodiment of the present invention features a two-dimensional array of modifications 102 to a surface 104 of the plate structure 100. The implantable plate structure 100 of the preferred embodiment of FIG. 4 features a readable portion 106 shown in FIG. 4 to be integral with a main portion 108 of an implant device 110. Alternatively, the readable portion 106 of the implant device 110 may be disposed upon the main portion 108 of the implant device 110. The readable portion 106 may be coupled to the main portion 108 by such means as fasteners or adhesives or through interference fit. The modifications 102 to the surface 104 of the plate structure 100 shown in FIG. 4 are holes 112 that are micromanufactured through the surface 104 of the plate structure 100. The plate structure 100 may be composed of any material such as a metal, polymer, or ceramic compatible with the imaging modality selected.

The preferred embodiment shown in FIG. 4 features a plate structure 100 that is one centimeter squared and one millimeter thick and has a seven-by-seven array of holes 112. The holes 112 are spaced about one millimeter from each other to provide 49 bits. After subtracting bits used for error correction, approximately four trillion reliable database entry fields with error correction are provided by the seven-by-seven array of holes 112. A separate database entry field for every human on Earth requires an implantable device having 33 bits of data—sufficient to uniquely identify over 8 billion cases. An additional eight bits is needed if each person on Earth were allocated up to 256 implants each. A Hamming code is implemented in the preferred embodiment of the implantable device with an additional eight bits to provide for the detection and correction of single bit errors.

Figure 5:
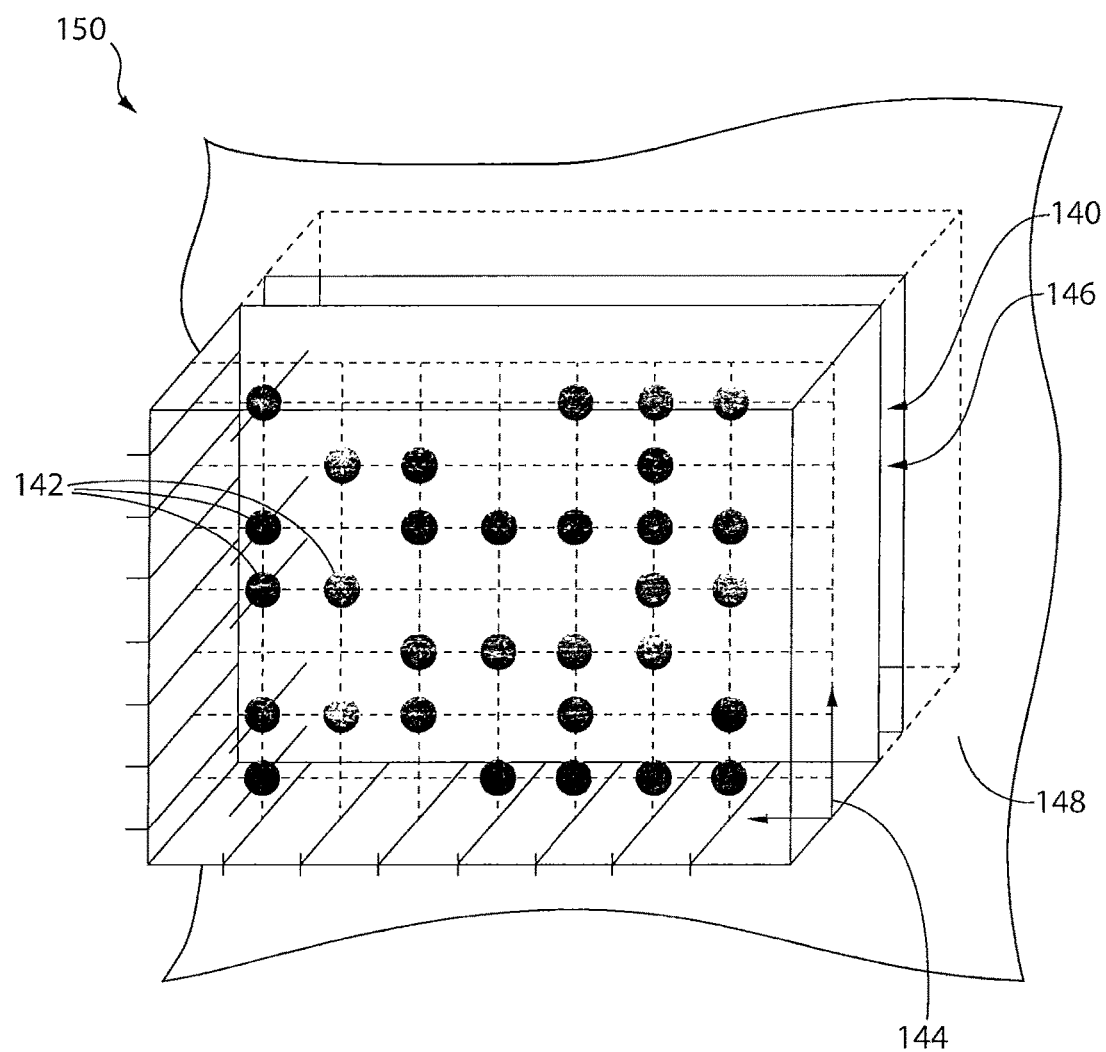
FIG. 5 is a front perspective view of a micromanufactured identifiable implant device in accordance with further aspects of the present invention.

Referring now to FIG. 5, an implantable plate structure 140 of a preferred embodiment of the present invention features a two-dimensional array of embedded markers 142 located at an internal plane 144 of the implantable plate structure 140. The embedded markers 142 of the preferred embodiment are internal volumes of a second material of different density. The implantable plate structure 140 of FIG. 5 features a readable portion 146 shown in FIG. 5 to be disposed upon a main portion 148 of an implant device 150. Although not shown in FIG. 5, the readable portion 146 may be coupled to the main portion 148 by such means as fasteners or adhesives or through interference fit. Alternatively, the readable portion 146 of the implant device 150 may integral with the main portion 148 of the implant device 150. The second material having a different density than the plate structure shown in FIG. 5 may be a substance of any material phase including a solid, liquid, or a gas. The embedded markers 142 as an array of internal volumes of FIG. 5 may also be voids in the material of the readable portion 146 of the implantable plate structure 140. The implantable plate structure 140 may be composed of any material such as a metal, ceramic, or polymer.

Similar to the plate structure of FIG. 4, the preferred embodiment shown in FIG. 5 features a plate structure 140 that is one centimeter squared and one millimeter thick and has a seven-by-seven array of internal volumes or voids forming embedded markers 142. The volumes are spaced about one millimeter from each other to provide 49 bits. After subtracting bits used for error correction, four trillion reliable database entry fields with error correction are provided by the seven-by-seven array of volumes or voids. A separate database entry field for every human on Earth requires an implantable device having 33 bits of data. An additional eight bits is needed if each person on Earth were allocated up to 256 implants each. A Hamming code is implemented in the preferred embodiment of the implantable device with an additional eight bits to provide for the detection and correction of single bit errors.

Figure 6:
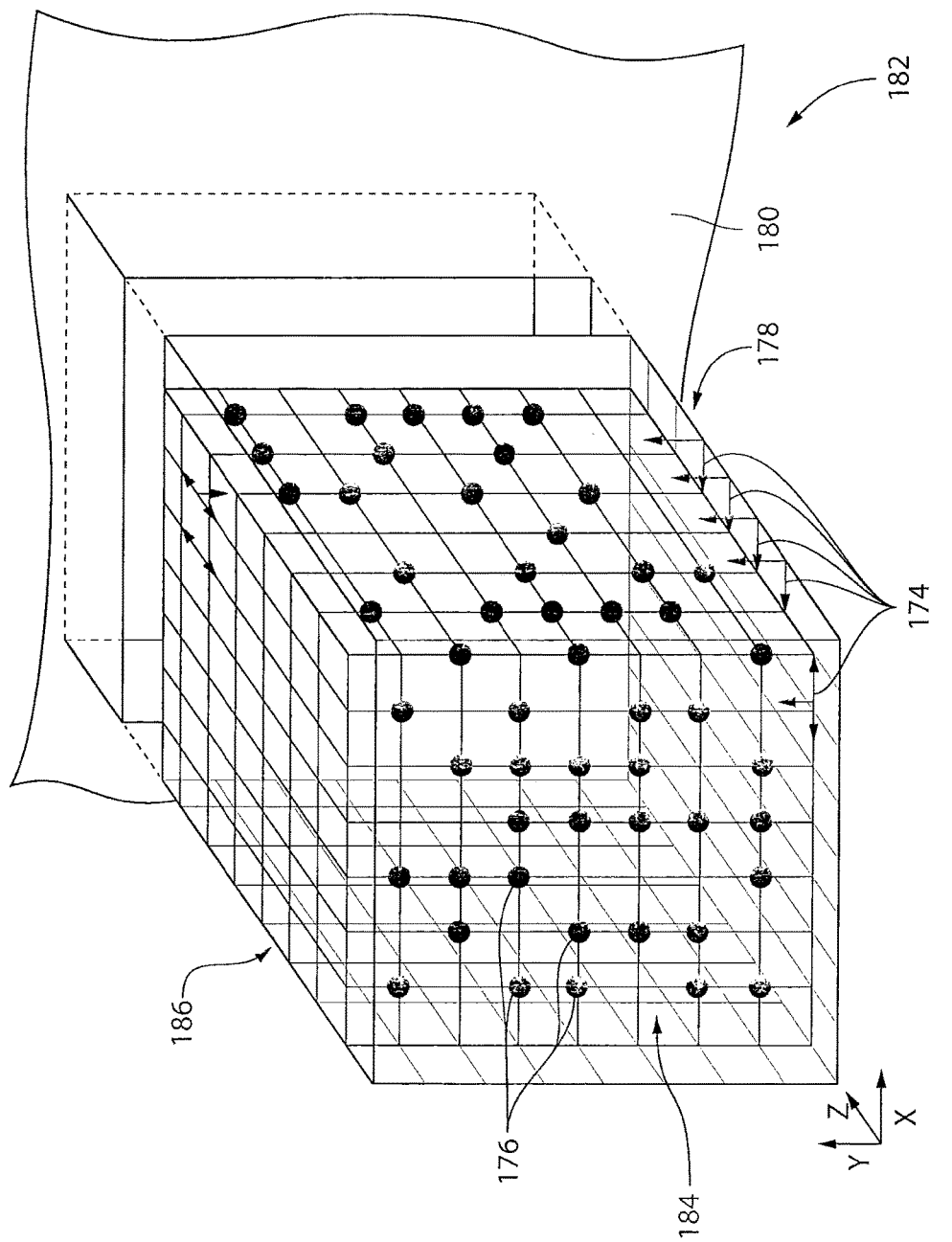
FIG. 6 is a front perspective view of a micromanufactured identifiable implant device in accordance with further aspects of the present invention.

Referring now to FIG. 6, an implantable structure 170 of a preferred embodiment of the present invention features a three-dimensional array 186 of embedded markers 176 located on a series of internal planes 174 of the implantable structure 170 that are separated across the z-axis of the implantable structure 170. Each of the internal planes 174 shown in FIG. 6 comprise a three-dimensional array of embedded markers 176. The embedded markers 176 in the preferred embodiment are internal volumes of a second material of differing density than a first material forming the remainder of the implantable structure 170. The embedded markers 176 may additionally be composed of a material differing from both the first and second materials forming an identifiable implant device having three or more materials, similar to the implant device shown in FIG. 3. This material modulation further increases the density of data recorded in the implant structure 170.

The implantable structure 170 of the preferred embodiment of FIG. 6 features a readable portion 178 shown in FIG. 6 to be disposed on a main portion 180 of an implant device 182. Although not shown in FIG. 6, the readable portion 178 may be coupled to the main portion 180 by such means as fasteners or adhesives or through interference fit. Alternatively, the readable portion 178 of the implant device 182 may be integral with the main portion 180 of the implant device 182. The second material having a different density than the implantable structure 170 shown in FIG. 6 may be a substance of any material phase including a solid, liquid, or a gas. The array of internal volumes of FIG. 6 forming embedded markers 176 may also be voids in the material of the readable portion 178 of the implantable structure 170. The implantable structure 170 may be composed of any material such as a metal, ceramic, or polymer.

As with the embodiment shown in FIG. 5, each plane 174 in the three-dimensional array 186 of the preferred embodiment shown in FIG. 6 features a unique seven-by-seven two-dimensional array 184 of embedded markers 176. The implantable structure 170 of FIG. 6 features the seven unique two-dimensional arrays 184 along the planes 174 such that the seven-by-seven-by-seven three-dimensional array 186 is formed. Data is extracted from the three-dimensional array 186 shown in FIG. 6 through volume imaging used with an extraction algorithm and advanced error correction coding in three dimensions. Due to the large amount of data within the internal array 186 of the implantable structure 170 shown in FIG. 6, external databases would not be required to access detailed implant manufacturing information, patient records, surgery data, or other related medical records. Through image analysis, medical staff would have immediate access to medical records encoded entirely within the implant device 182.

Figure 7:
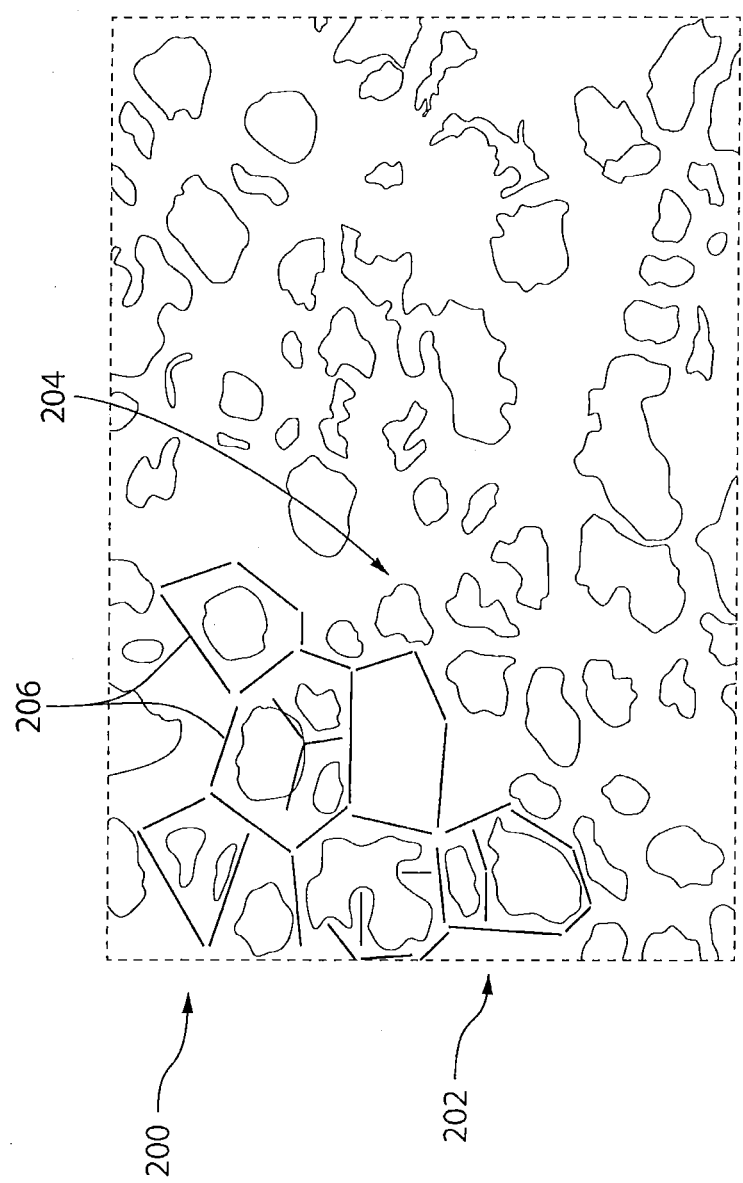
FIG. 7 is an enlarged cross sectional view of a micromanufactured identifiable implant device in accordance with further aspects of the present invention.
Figure 7A:
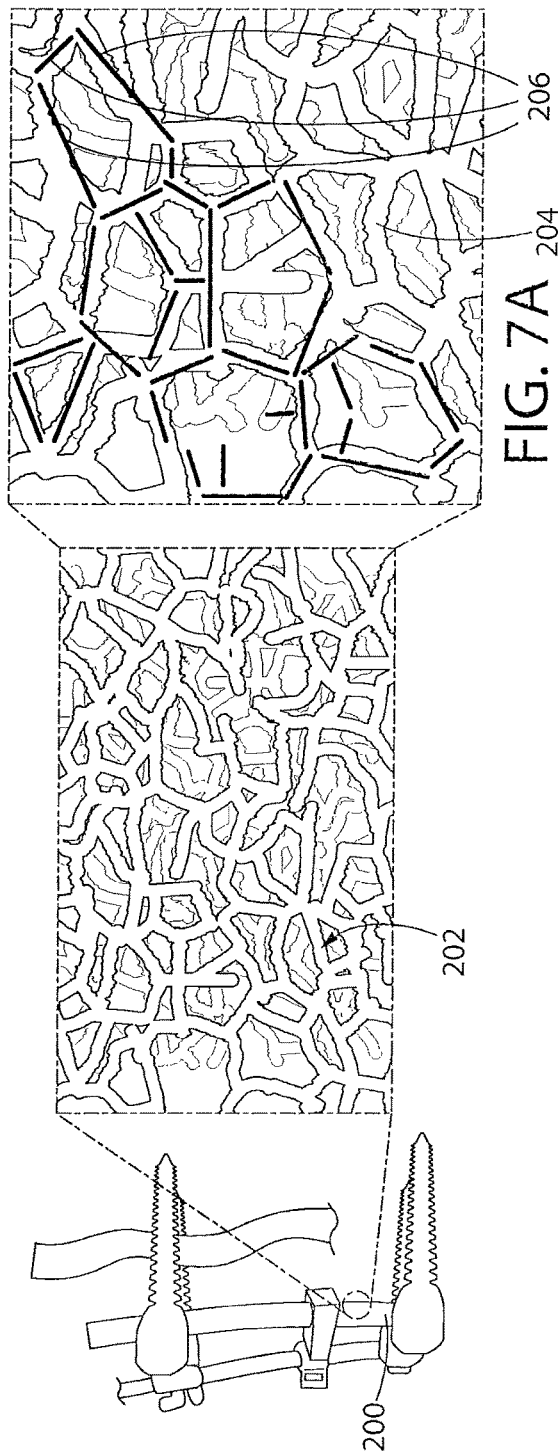
FIG. 7A is an enlarged cross sectional view of a micromanufactured identifiable implant device in accordance with further aspects of the present invention.
Figure 8A:
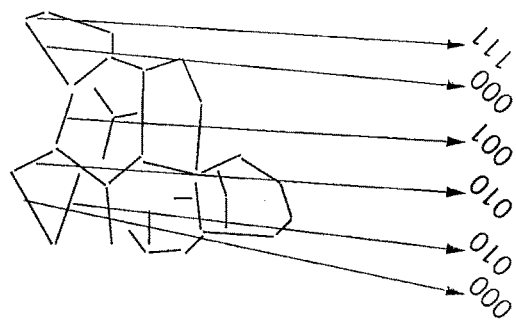
FIG. 8A is a diagram relating to indicia data of a micromanufactured identifiable implant device in accordance with further aspects of the present invention.
Figure 8:
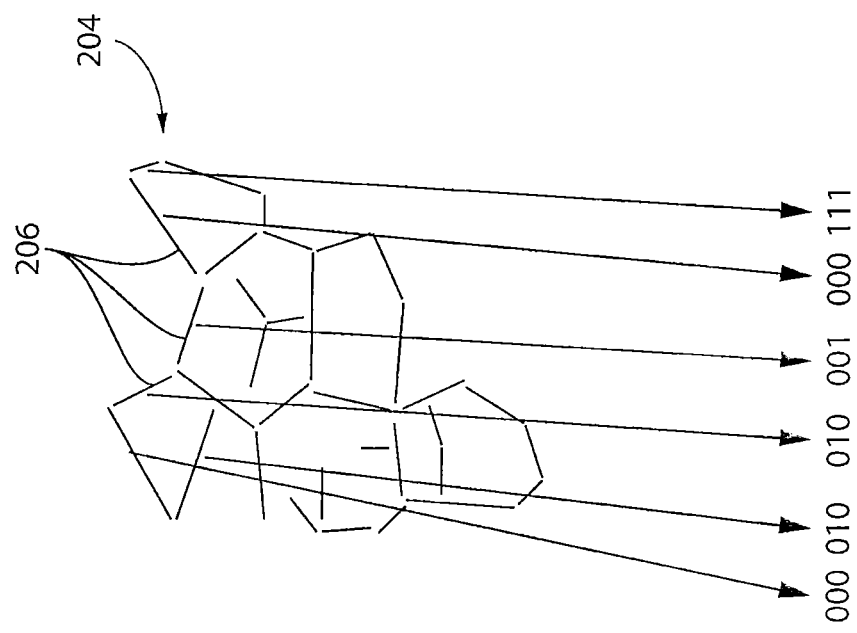
FIG. 8 is a diagram relating to indicia data of a micromanufactured identifiable implant device in accordance with further aspects of the present invention.

Reference is now made to FIG. 7, which shows an implantable structure 200 of a preferred embodiment of the present invention. The implantable structure 200 of the preferred embodiment is a metal mesh structure fabricated using additive manufacturing (also known in the art as 3D printing). The Materials Science & Engineering article titled "Characterization of Ti-6AI-4V Open Cellular Foams Fabricated by Additive Manufacturing Using Electron Beam Melting" by Murr, et al. discusses such additive manufacturing methods to produce such exemplary structures as are displayed in the article, and is incorporated herein by reference. Through an AM manufacturing process, a unique internal structure is formed while maintaining the structural requirements of the implant device 200. A readable portion 202 includes an internal structure 204 inside the readable portion 202. The internal structure 204 includes linking structures 206 that interconnect to form the internal structure 204. Individual linking structures 206 in the preferred embodiment shown in FIG. 7 each have a predetermined size and orientation in reference to a unique registration structure that would be included in every implant and easily identifiable. As shown in FIG. 8, the size and orientation of a particular linking structure 206 of the preferred embodiment of the present invention is predetermined to represent binary data. As with the embodiments of the present invention shown in FIGS. 1-6, the data is read to gather valuable information relating to the implant, patient, surgical operation, etc. The data contained in the readable portion 202 of the implantable structure 200 can be accurately read through non-invasive means such as x-ray, fluoroscopy, computed tomography, electromagnetic radiation, ultrasound, and magnetic resonance imaging. FIGS. 7A and 8A show, in detail, the readable portion 202, internal structure 204, and linking structure 206 of the implantable structure 200 according to one embodiment of the present invention.

One or more of the embodiments of the present invention are structurally encoded devices, which refers to the 3D encoding of digital information in a structure as variations in geometric or physical features—widths, densities, color, feature angles, etc. Bar codes are an example of a 2D encoding of digital information with modulations of color (dark versus light) with varying widths of printed bars on a surface. A typical embodiment of the structurally encoded devices of the present invention may contain data that is not readily apparent to a viewer of the device structure. Further, encoding of the typical embodiments of the present invention is handled by physical means other than those accomplished through circuitry, electromagnetic or other, within the implant device itself or through a type of internal storage means such as magnetic storage means or the like. Such structurally encoded devices, as disclosed herein and described in relation to the typical and/or preferred embodiments of the present invention allow simplified production, maintenance, and/or operation costs for identification, storage, and/or retrieval of unique implant data while retaining a substantial amount of information with reduced probability for error.

The preferred embodiments of the present invention, as shown individually in FIGS. 1-9, may be manufactured by one or more of the AM processes described above. The method of manufacturing an identifiable implant according to a preferred embodiment of the present invention comprises providing a main portion of an identifiable implant device, providing a readable portion of an identifiable implant device, printing a first material onto a first readable portion surface to create a first printed layer, and printing the first material onto the first printed layer to create a second printed layer. At least one of the printing of the first material onto the first readable portion surface and the printing of the first material onto the first printed layer comprises printing encoded indicia. Further, the encoded indicia may comprise volumes of a second material having a different density than the first material found elsewhere in the readable portion of the identifiable implant device. As an example, the readable portion of an identifiable implant may be formed by an AM or 3D printing process such that micro-volumes of a metal material having a relatively high density are deposited within a polymer substrate having a relatively low density. The encoded indicia may also comprise voids in the first material of the identifiable implant device. Further, any single embodiment of the present invention may be manufactured using a combination of traditional manufacturing processes and additive manufacturing processes. For example, a 3D printed implant device with internal indicia formed by the 3D printing process may also have a series of notches micromachined onto an exterior surface of the 3D printed implant device.

The identifiable implant device of the present invention enables more accurate reporting, reviewing, and analyzing of adverse event reports so that problem devices can be identified and corrected more quickly. Additionally, the identifiable implant device of the present invention reduces medical error by enabling health care professionals and others to rapidly and precisely identify a device and obtain important information concerning the characteristics of the device. The present invention enhances analysis of devices on the market by providing a standard and clear way to document device use in electronic health records, clinical information systems, claim data sources, and registries. Through the identifiable implant device of the present invention, a more robust post-market surveillance system may also be leveraged to support premarket approval or clearance of new devices and new uses of currently marketed devices. The present invention further provides a standardized identifier that will allow manufacturers, distributors, and healthcare facilities to more effectively manage medical device recalls. Moreover, the present invention provides a foundation for a global, secure distribution chain, helping to address counterfeiting and diversion and prepare for medical emergencies. The identifiable implant device of the present invention enables development of a medical device identification system that is recognized around the world.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A method of identifying an implant device, comprising:
    discerning indicia by at least one of x-ray, fluoroscopy, computed tomography, electromagnetic radiation, ultrasound, and magnetic resonance imaging, said indicia comprising a plurality of modifications to at least one surface of a detectable element disposed within said implant device, wherein at least one of said plurality of modifications is a void;
    accessing records associated with at least one of a plurality of implantable devices; and
    providing information associated with said implant device based on said indicia and said records.

2. The method of claim 1, further comprising:
    displaying said information associated with said implant device based on said indicia and said records through a user interface.

3. The method of claim 1, wherein a readable portion comprises said indicia and is disposed upon a main portion of said implant device.

4. The method of claim 1, wherein said plurality of modifications to at least one surface of the detectable element comprises a Hamming code.

5. The method of claim 1, wherein said indicia further comprise a plurality of detectable elements disposed within said implant device as an array of embedded markers.

6. The method of claim 1, wherein said information comprises at least one of manufacturer information, patient information, surgeon information, and surgical procedure information.

7. An implant device identifiable after implantation comprising:
    an implant body defining a plurality of linking structures, wherein each of said linking structures has at least one of a predetermined size and predetermined orientation, said plurality of linking structures being interconnected to substantially form an implant device structure, and said plurality of linking structures forming predetermined indicia such that said predetermined indicia are discernible by at least one of x-ray, fluoroscopy, computed tomography, electromagnetic radiation, ultrasound, and magnetic resonance imaging, and further wherein at least one of said linking structures is comprised of a material that is different than a second at least one of said linking structures, and further wherein at least one of said predetermined indicia is a void.

8. The implant device of claim 7, further comprising a main portion of said implant device and a readable portion of said implant device, wherein said readable portion is integral with said main portion.

9. The implant device of claim 7, further comprising a main portion of said implant device and a readable portion of said implant device, wherein said readable portion is disposed upon said main portion.

10. The implant device of claim 7, wherein said predetermined indicia in said implant device comprise a Hamming code.

11. The implant device of claim 7, wherein said predetermined indicia comprise at least one of manufacturer information, patient information, surgeon information, and surgical procedure information.

12. The implant device of claim 7, wherein said predetermined indicia is compressed.

13. The implant device of claim 7, wherein said predetermined size and predetermined orientation of said linking structures correspond to a unique registration structure.

14. The implant device of claim 7, wherein said predetermined size and predetermined orientation of said linking structures represent binary data.

15. An implant device identifiable after implantation, comprising:
    an implant body comprising indicia, wherein said indicia are formed by a plurality of modifications within the implant body, such that said indicia are discernible by at least one of x-ray, fluoroscopy, computed tomography, electromagnetic radiation, ultrasound, and magnetic resonance imaging from a perspective substantially perpendicular to said plane, and further wherein at least one of said plurality of modifications is a void.

16. The implant device of claim 15, wherein said indicia are discernible only from a perspective substantially perpendicular to said plane.

17. The implant device of claim 15, wherein said indicia are not discernible from a perspective parallel to said plane.

18. The implant device of claim 15, wherein said indicia comprises a code.

19. The implant device of claim 18, wherein said code is a Hamming code.

20. The implant device of claim 15, wherein the indicia comprise at least one of manufacturer information, patient information, surgeon information, and surgical procedure information.

* * * * *